United States Patent [19]

Aslam et al.

[11] Patent Number: 5,210,278
[45] Date of Patent: May 11, 1993

[54] PROCESS FOR THE PREPARATION OF BISARYLALKYL ETHERS

[75] Inventors: Mohammad Aslam, Corpus Christi, Tex.; Brad L. Smith, Matthews, N.C.; George Kvakovszky, Corpus Christi, Tex.

[73] Assignee: Hoechst Celanese Corporation, Del.

[21] Appl. No.: 934,995

[22] Filed: Aug. 25, 1992

Related U.S. Application Data

[62] Division of Ser. No. 701,407, May 14, 1991.

[51] Int. Cl.$^5$ .................. C07C 67/293; C07C 41/09
[52] U.S. Cl. .................. 560/138; 560/144; 568/586; 568/644; 568/645; 568/656; 568/659; 568/661
[58] Field of Search ............... 560/144, 138; 568/586, 568/644, 645, 656, 659, 661

[56] References Cited

U.S. PATENT DOCUMENTS

| | | | |
|---|---|---|---|
| 3,668,409 | 5/1972 | Schroder | 568/656 |
| 4,521,635 | 6/1985 | Stevens | 568/659 |
| 4,521,636 | 6/1985 | Kriel | 568/659 |
| 4,868,256 | 9/1989 | Aslam et al. | 526/75 |
| 4,868,257 | 9/1989 | Aslam et al. | 526/75 |
| 4,927,956 | 5/1990 | Vicari et al. | 560/130 |
| 4,933,495 | 6/1990 | Aslam et al. | 568/309 |
| 4,965,400 | 10/1990 | Vicari et al. | 560/130 |

OTHER PUBLICATIONS

Corson et al., 23, *J. Org. Chem.*, pp. 544–549, (1958).

*Primary Examiner*—José G. Dees
*Assistant Examiner*—Vera C. Clarke
*Attorney, Agent, or Firm*—James J. Mullen; Donald R. Cassady

[57] ABSTRACT

A process for preparing a substituted styrene by reacting a bisarylalkyl ether in the presence of an acid catalyst is disclosed. The process is preferably used for the preparation of 4-acetoxystyrene from 4,4'-(oxydiethylidene)bisphenol diacetate and 4-methoxystyrene from 4,4'-(oxydiethylidene)bisphenol dimethyl ether. A process for preparing a bisarylalkyl ether by reacting a corresponding arylalkanol in the presence of an acid catalyst is also disclosed.

14 Claims, No Drawings

PROCESS FOR THE PREPARATION OF BISARYLALKYL ETHERS

This is a division of application Ser. No. 07/701,407 filed May 14, 1991.

TECHNICAL FIELD OF THE INVENTION

The present invention relates to the field of substituted styrenes and, more particularly, to a process for the preparation thereof from bisarylalkyl ethers and a process for the preparation of such bisarylalkyl ethers from arylalkanols. Still more particularly, the present invention discloses a method of preparing 4-acetoxystyrene and 4-methoxystyrene from 4,4'-(oxydiethylidene)-bisphenol diacetate, and 4,4'-(oxydiethylidene)bisphenol dimethyl ether, respectively. Furthermore, the present invention discloses a method of preparing 4,4'-(oxydiethylidene)bisphenol diacetate and 4,4-(oxydiethylidene)bisphenol dimethyl ether from 4-acetoxyphenylmethylcarbinol and 4-methoxyphenylmethylcarbinol, respectively.

BACKGROUND OF THE INVENTION

Substituted styrenes are known compounds which are used in the production of photoresists, adhesives, coating compositions, pharmaceuticals, ultraviolet-absorbing sunscreen agents and other like compounds. More particularly, they are used as intermediate monomers for the production of polymers used for the preparation of said compounds.

A well known substituted styrene compound is 4-acetoxystyrene. The monomer 4-acetoxystyrene is a stable monomer which can be readily polymerized and copolymerized to low, medium and high molecular weight polymers. The monomer readily polymerizes in solution, suspension, emulsion or bulk using well-known free radical catalysts such as, for example, the peroxide and azo compounds. Such polymerization can take place in the absence of comonomers whereby the resultant product is a homopolymer or in the presence of comonomers whereby the resultant product is a copolymer. Examples of processes used for the production of homopolymers or copolymers of 4-acetoxystyrene are the processes disclosed in U.S. Pat. Nos. 4,822,862, 4,912,173 and 4,962,147. Other well-known processes can also be used.

In the case of copolymerization, the most commonly used comonomer is styrene. Other comonomers include vinyltoluene; alpha-methylstyrene; ortho-, meta-, and para- cloro- and bromostyrene; the diene monomers such as butadiene, the acrylate and methacrylate ester monomers such as methyl acrylate, ethyl acrylate, butyl acrylate, butyl methacrylate and 2-ethylhexyl acrylate; acrylonitrile; methacrylonitrile; the polymerizable acids such as acrylic acid, methacrylic acid, maleic acid, fumaric acid and the like; and the allyl ester comonomers described in U.S. Pat. No. 4,877,843. The homopolymers and the copolymers of 4-acetoxystyrene can be hydrolyzed to produce homopolymers and copolymers of 4-hydroxystyrene which are well-known compositions used in the manufacturing of metal treatment compositions, photoresists, epoxy resins and epoxy resin curing agents. Processes for the conversion of homopolymers and copolymers of 4-acetoxystyrene to homopolymers and copolymers of 4-hydroxystyrene are disclosed in U.S. Pat. Nos. 4,678,843, 4,689,371, 4,822,862, 4,857,601, 4,877,843, 4,898,916, 4,912,173, and 4,962,147.

Several methods have been developed for the production of the monomer 4-acetoxystyrene. Corson, et al., *Preparation of Vinylphenols and Isopropenylphenols*, 23 J. Org. Chem. 544-549 (1958), discloses a process for making 4-acetoxystyrene from phenol. According to the process, phenol is acylated to 4-hydroxyacetophenone which is then acetylated to 4-acetoxyacetophenone. The latter compound is hydrogenated to 4-acetoxyphenylmethylcarbinol, which is, then, dehydrated to 4-acetoxystyrene. Another process for the preparation of 4-acetoxystyrene is disclosed in copending U.S. patent application Ser. No. 07/548,170, now U.S. Pat. No. 5,041,614, which is incorporated herein and is made part hereof by reference. In that process, 4-acetoxyphenylmethylcarbinol is dehydrated in the presence of acetic anhydride and an acid catalyst to form 4-acetoxystyrene. The compound 4-acetoxyphenylmethylcarbinol is sometimes referred to herein for brevity and convenience as "APMC."

Copending U.S. patent application Ser. No. 07/598,510, now U.S. Pat. No. 5,151,546, discloses methods of preparing APMC. One method involves heating 4-acetoxyacetophenone at a temperature of from about 54° C. to about 120° C. and at a pressure of about 14.7 psig to about 5000 psig in the presence of at least a stoichiometric amount of hydrogen and a catalyst selected from the group consisting of Pd/C or activated nickel in the absence of a solvent. Another method involves the hydrogenation of 4-acetoxyacetophenone with a suitable reagent such as $NaBH_4$, lithium aluminum hydride, hydrogen and diisobutyl aluminum hydride in the presence of a solvent.

Another method of preparing 4-acetoxystyrene is disclosed in copending U.S. patent application Ser. No. 07/598,510 which is incorporated herein and is made part hereof by reference. APMC is dehydrated in the presence of a dehydrating agent such as $KHSO_4$, alumina, titania, silica gel and mineral acids. The reaction is carried out under substmospheric conditions at a temperature in the range of 85° C. to 300° C. for about 0.2 to about 10 minutes.

Examples of other substituted styrene derivatives are disclosed in U.S. Pat. Nos. 4,868,256; 4,868,257; 4,933,495; 4,927,956 and 4,965,400. U.S. Pat. Nos. 4,868,256; 4,868,257 and 4,933,495 disclose methods for producing substituted styrenes and, more particularly, 3-mono or 3,5-disubstituted acetoxystyrene by dehydrating 1-(3'-mono or 3',5'-disubstituted-4'-acetoxyphenyl) ethanol with an acid or a base and hydrolyzing said product to produce 3-mono or 3,5-disubstituted hydroxystyrene. The substituents are selected from the group consisting of Cl, Br, I, $NO_2$, $NH_2$, $SO_3H$ or $C_1$–$C_{10}$ alkyl. Furthermore, those patents disclose a method of producing 3-bromo-4-acetoxy-5-methylstyrene from 1-(3'-bromo-4'-acetoxy-5'-methylphenyl)ethanol.

U.S. Pat. No. 4,927,956 discloses 3,5-disubstituted-4-acetoxystyrene wherein the substitution is independently $C_1$ to $C_{10}$ alkyl or alkoxy or amino; and substituted 4-hydroxy- and 4-acetoxystyrene compounds wherein the substitutes in the 2,3 and 6- positions are independently hydrogen, alkyl, alkoxy or halogen and the substitute in the 5-position is chlorine or bromine.

U.S. Pat. No. 4,965,400 is directed to a method of preparing 3,5-disubstituted-4-acetoxystyrene by dehydrating 1-(3',5'-disubstituted-4'-acetoxyphenyl)ethanol wherein each of the 3,5-substitutions are independently C₁ to C₁₀ alkyl or alkoxy, amino or halogen. The reaction is carried out in the presence of an acid dehydrating agent.

Although several methods were employed in the past for the preparation of substituted styrenes, none of those methods involved the preparation of such substituted styrenes from bisarylalkyl ethers such as 4,4'-(oxydiethylidene)-bisphenol diacetate or 4,4'-(oxydiethylidene)bisphenol dimethyl ether.

4,4'-(oxydiethylidene)bisphenol diacetate which is otherwise identified as bis (4-acetoxyphenylmethylcarbinol) ether is sometimes referred to herein for brevity and convenience as "APMC-Ether." The compound 4,4'-(oxydiethylidene)bisphenol dimethyl ether which is otherwise identified as (4-methyoxyphenylmethylcarbinol) ether is sometimes referred to herein for brevity and convenience as "MPMC-Ether."

APMC-Ether is a compound isolated from a species of mushrooms as disclosed in F. Bohlmann et al., Phytochemistry 18(8), 1403 (1979). Furthermore, APMC-Ether is formed as an impurity in the acid catalyzed dehydration of APMC to 4-acetoxystyrene monomer and in the thermal treatment of APMC during its purification.

In the past, there were no uses for APMC-Ether, Accordingly, APMC-Ether removed from mixtures containing it as an impurity required disposal in landfills or similar disposal sites thereby giving rise to economic and environmental burdens. According to the present invention, APMC-Ether is used to produce 4-acetoxystyrene whereby the aforesaid economic and environmental burdens are eliminated.

In addition to disclosing a method of preparing substituted styrene derivatives from bisarylalkyl ethers, the present invention discloses a method of preparing such bisarylalkyl ethers from corresponding arylalkanols. Such method is preferably used for the preparation of APMC-Ether from APMC and for the preparation of MPMC-Ether from 4-methoxyphenylcarbinol which is sometimes referred to herein for brevity and convenience as "MPMC." No such method was disclosed by the prior art.

These and other advantages of the present invention will become apparent from the following description.

SUMMARY OF THE INVENTION

A bisarylalkyl ether such as APMC-Ether or MPMC-Ether is heated in the presence of an acid catalyst to produce a substituted styrene such as 4-acetoxystyrene or 4-methoxystyrene, respectively. The reactant which is in the liquid phase is heated to a temperature of about 160° C. to about 230° C. to convert the bisarylalkyl ether to the substituted styrene by cleavage and dehydration. The reaction is preferably carried out under subatmospheric conditions to effect the immediate vaporization and removal of the substituted styrene product from the reactor to prevent the polymerization of such product. The reaction is carried out preferably in the presence of a free radical inhibitor which inhibits the free radical polymerization of the substituted styrene product. In the case of the preparation of 4-acetoxystyrene from APMC-Ether, the reaction is preferably carried out also in the presence of acetic anhydride to prevent the hydrolysis of 4-acetoxystyrene to 4-hydroxystyrene.

A method of preparing a bisarylalkyl ether from a corresponding arylalkanol through the condensation of the arylalkanol in the presence of an acid catalyst is also disclosed. Such method is preferably used for the preparation of APMC-Ether from APMC and for the preparation of MPMC-Ether from MPMC. The arylalkanol reactant is heated to a temperature of about 80° C. to about 120° C. in the presence of the catalyst. The reaction is preferably carried out under subatmospheric pressure to effect the rapid removal of the water coproduct of the reaction. Such removal causes an increase in the yield and selectivity to the bisarylalkyl ether.

DETAILED DESCRIPTION OF THE INVENTION

(a) Preparation of Substituted Styrenes from Bisarylalkyl Ethers

According to the present invention, a process for the production of a substituted styrene is disclosed by heating a bisarylalkyl ether in the presence of an acid catalyst. One equivalent of the bisarylalkyl ether is cleaved and dehydrated to produce two equivalents of substituted styrene. The substituted styrene produced in accordance of the present invention is of the formula:

(Formula 1):

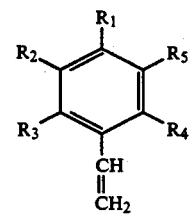

wherein R₁ is

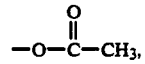

—O—CH₃, —O—CH₂—CH₃, halogen or NO₂; and R₂, R₃, R₄ and R₅ are independently hydrogen, halogen or C₁-C₄ alkyl.

The reactant bisarylalkyl ether is of the formula (Formula 2),

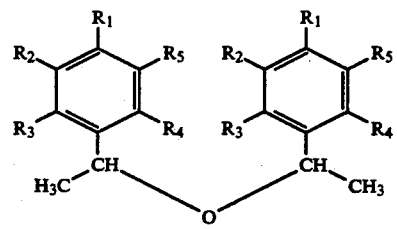

wherein R₁ is

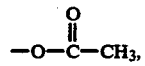

—O—CH₃, —O—CH₂—CH₃, halogen or NO₂; and R₂, R₃, R₄ and R₅ are independently hydrogen, halogen, or C₁-C₄ alkyl.

The reactant bisarylalkyl ether in its liquid phase is fed to a reactor. Therein, in the presence of the acid catalyst, it is heated to a temperature which is sufficiently high to effect the cleavage and dehydration of the reactant to form the substituted styrene but sufficiently low to minimize the tendency of the components of the reaction mass for polymerization. Accordingly, the reaction is carried out at temperatures in the range of about 120° C. to about 230° C. and, preferably, in the range of about 160° C. to about 220° C. The reaction mass is continuously stirred by well known stirring means to maintain the homogeneity thereof.

Because the substituted product readily polymerizes under the temperature conditions encountered in the reaction, it is preferred that the product be removed immediately from the reaction mass via evaporation. Accordingly, the reaction is carried out under subatmospheric conditions, preferably in the range of about 0.5 mm Hg to about 100 mm Hg, to effect the immediate vaporization and removal of the product from the reaction mass. The vaporized product is cooled and condensed in a condenser and is collected as a liquid product in an overhead receiver.

The conversion of the bisarylalkyl ether to substituted styrene in accordance with the present invention is relatively fast. In the case of the conversion of APMC-Ether, for example, the conversion typically takes place in about less than one second to about 15 minutes depending on feed rate to the reactor, mixing conditions and temperature.

The reaction may be carried out in a batch mode, a continuous mode or a combination thereof such as a continuous fed-batch mode. In the continuous fed-batch mode, reactant and catalyst are continuously fed to the reactor, the substituted styrene product is continuously removed by evaporation and the residue and the catalyst are allowed to build up in the reactor until the end of the cycle.

Any one of the acid catalysts may be used to carry out the reaction of the present invention. Such catalysts include, but are not limited to, phosphoric acid, p-toluenesulfonic acid, methanesulfonic acid, ammonium bisulfate and potassium bisulfate. The amount of catalyst required varies from catalyst to catalyst. In all instances, however, the amount is very small as compared to the amount of reactant. In the case of the conversion of APMC-Ether to 4-acetoxystyrene, for example, the amount of catalyst is usually less that one (1) mole of catalyst per 100 moles of reactant APMC-Ether.

In accordance with the present invention, the reaction is typically carried out stoichiometrically as follows (Reaction 1):

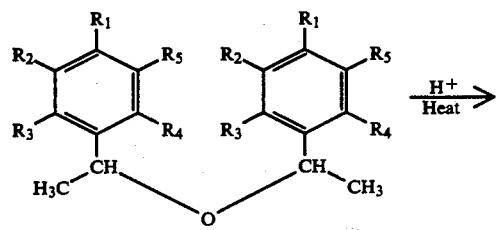

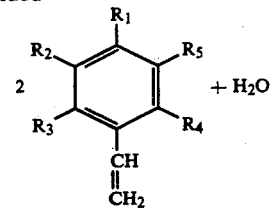

wherein $R_1$ is

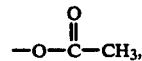

—O—$CH_3$, —O—$CH_2$—$CH_3$, halogen or $NO_2$; and $R_2$, $R_3$, $R_4$ and $R_5$ are independently hydrogen or $C_1$-$C_4$ alkyl.

In the case of converting, a bisarylalkyl ether of Formula 2 wherein $R_1$ is

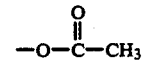

(acetoxy) to a corresponding acetoxy-substituted styrene, although the reaction can be carried out in the absence of acetic anhydride, it is preferred that acetic anhydride be fed to the reactor together with the reactant acetoxy-containing bisarylalkyl ether to prevent the hydrolysis of the acetoxy-containing substituted styrene product to a corresponding hydroxy-containing compound. For example, in the case of APMC-Ether conversion to 4-acetoxystyrene, it is preferred that acetic anhydride be fed to the reactor together with the reactant APMC-Ether to prevent the hydrolysis of the 4-acetoxystyrene product to 4-hydroxystyrene. The amount of acetic anhydride may be as high as about five (5.0) moles of acetic anhydride per one (1) mole of reactant APMC-Ether with the preferred amount being 0.05 moles of acetic anhydride per one (1) mole of reactant APMC-Ether. When the reaction is carried out in the absence of acetic anhydride, one (1) mole of APMC-Ether is converted to two (2) moles of 4-acetoxystyrene and one (1) mole of water in a reaction represented stoichiometrically as follows:

(Reaction 2):

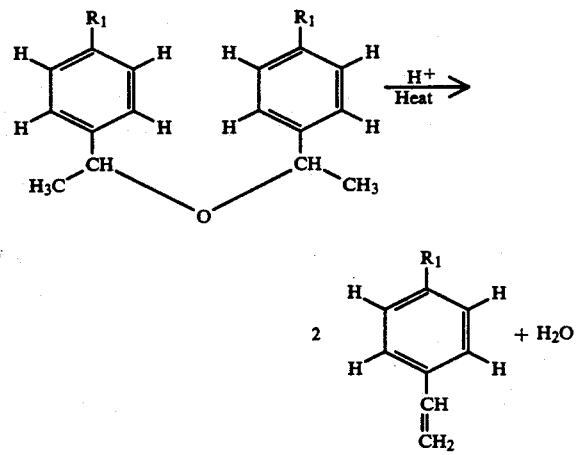

-continued wherein $R_1$ is $-O-\overset{\overset{O}{\|}}{C}-CH_3$.

When the reaction is carried out in the presence of acetic anhydride the APMC-Ether reacts stoichiometrically with the acetic anhydride in accordance with the following reaction (Reaction 3):

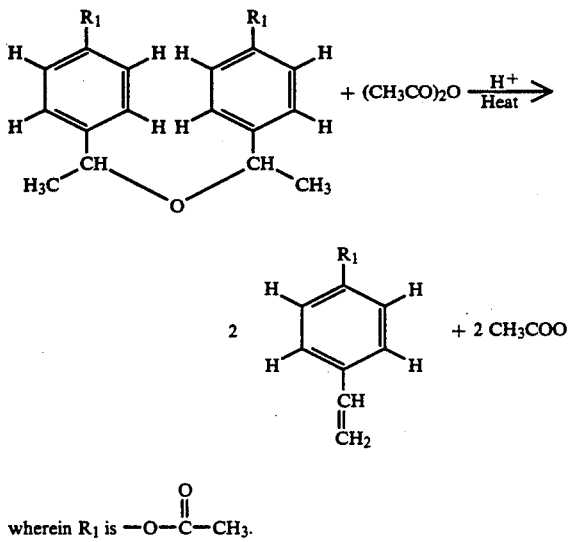

wherein $R_1$ is $-O-\overset{\overset{O}{\|}}{C}-CH_3$.

If the amount of acetic anhydride available for the reaction is less than the stoichiometric amount shown in Reaction 3, i.e., one (1) mole of acetic anhydride per one (1) mole of APMC-Ether, the APMC-Ether which is not converted by Reaction 3 is converted by Reaction 2.

In order to minimize the free radical polymerization of the substituted styrene product such as 4-acetoxystyrene or 4-methoxystyrene, it is preferred that a free radical inhibitor be used in the reaction to inhibit polymerization. Any known inhibitors such as phenothiazine, t-butyl catechol or the like that effect such quenching may be used. The use of the inhibitor, however, is not necessary for the reaction of the present invention to be carried out.

(b) Preparation of Bisarylalkyl Ethers from Arylalkanols

As discussed in the Background of the Invention section hereof, the present invention discloses a method of preparing bisarylalkyl ether from corresponding arylalkanols. The reaction is represented as follows (Reaction 4):

-continued wherein $R_1$ is $-O-\overset{\overset{O}{\|}}{C}-CH_3$, $-O-CH_3$, $-O-CH_2-CH_3$, halogen or $NO_2$; and $R_2$, $R_3$, $R_4$ and $R_5$ are independently hydrogen, halogen or $C_1-C_4$ alkyl. The method is preferably used for the conversion of APMC to APMC-Ether and for the conversion of MPMC to MPMC-Ether.

The reactant arylalkanol is fed as liquid to a reactor together with an acid catalyst. The reactant and the catalyst are thoroughly mixed and heated to a temperature in the range of about 80° C. to about 120° C. which is sufficiently high to initiate and complete the condensation reaction shown as Reaction 4. At lower temperatures, the reaction is very slow and, at higher temperatures, the bisarylalkyl ether product such as AMPC-Ether or MPMC-Ether tends to decompose.

In order to increase the yield of arylalkanol to bisarylalkyl ether, it is preferred that the water product of the reaction be immediately removed. Accordingly, the reaction is carried out under subatmospheric conditions in the range of about 0.1 mm Hg to about 760 mm Hg to accomplish the immediate removal of the water through vaporization. The preferred pressure is in the range of about 0.1 mm Hg to about 50 mm Hg and the most preferred pressure is in the range of about 0.1 mm Hg to about 2 mm Hg.

An organic solvent may also be used to remove the water extensively and satisfactorily by codistilling the water with the solvent. The solvent may be recirculated to the reactor for further use. Examples of such solvent include, but are not limited to toluene and 1,2,4-trimethylbenzene.

Any acid catalyst may be used to carry out the reaction. Strong acid catalysts, however, such as sulfuric acid tend to promote the formation of polymers and other undesirable byproducts. Accordingly, weak acid catalysts are preferred. Examples of such catalyst include, but are not limited to potassium bisulfate, phosphoric acid, p-toluenesulfonic acid and ammonium bisulfate. The most preferred acid catalysts are those having a dissociation constant similar to the dissociation constant of potassium bisulfate, ($pKa \approx 2$ (relative to water)).

The amount of catalyst required varies depending on the reaction conditions and the type of the catalyst. In the case of potassium bisulfate with the reaction being carried at about 100° C., the preferred amount of catalyst is about 8 to about 9 weight percent of the total charge to the reactor.

The reaction is relatively slow and the reaction time is in the range of about 0.5 hours to about 8.0 hours depending on the reaction conditions, the catalyst and other factors. In a typical reaction wherein APMC is used to produce APMC-Ether in the presence of about 9 weight percent potassium bisulfate catalyst at about 100° C. and 0.25 mm Hg, the reaction time is from about 1.0 to about 4.0 hours.

Because the reaction time is relatively slow, the reaction is preferably carried out in a batch mode. A continuous mode, however, wherein reactants and catalyst are slowly fed to the reactor and products are slowly removed therefrom may be used.

The following examples further illustrate the invention but are not to be construed as limitations on the scope of the invention contemplated herein. Examples 1–3 demonstrate the conversion of APMC-Ether to 4-acetoxystyrene. Example 4 illustrates the conversion of MPMC-Ether to 4-methoxystyrene. Examples 5–7 illustrate the conversion of APMC to APMC-Ether. Example 8 illustrates the converstion of MPMC to MPMC-Ether. All calculations of conversions, selectivities and yields are based on moles of the compounds involved.

EXAMPLE 1

A flask heated by hot oil was fitted with a chilled water overhead condenser, a thermowell with a thermocouple, an overhead stirrer and a vacuum pump. Crude APMC-Ether (20 grams) containing 78.2 weight percent APMC-Ether, 7.2 weight percent APMC and 3.9 weight percent 4-acetoxyphenylmethylcarbinol acetate (sometimes referred to herein as "APMC-Acetate") was mixed in another flask with six (6.0) grams of acetic anhydride. Phosphoric acid (0.022 grams) having a concentration of 85 weight percent that corresponds to 0.32 moles of pure phosphoric acid per 100 moles of APMC-Ether was added to said mixture. The resultant mixture was fed to the hot flask at a rate of 1.2 grams per minute. The hot oil temperature was maintained at about 220° C. to about 230° C. and the reaction mass temperature in the hot flask was maintained at about 180° C. to about 200° C. The vacuum pump maintained a vacuum in the flask at about 80 mm Hg. 4-acetoxystyrene and acetic acid were produced in the hot flask.

The vacuum conditions caused the 4-acetoxystyrene and the acetic acid products to vaporize in the flask as soon as they were formed together with unreacted acetic anhydride. The vapors were condensed in the overhead condenser and collected in an overhead receiver. The residue and the catalyst were allowed to build up in the hot flask and were discarded after the cycle was completed.

At the end of the reaction, the total amount of residue removed from the flask was 9.3 grams and the product collected in the overhead receiver was 15.6 grams. The overhead product contained 54.6 weight percent 4-acetoxystyrene. The conversion of the crude APMC-Ether was 99.6 percent with the selectivity to 4-acetoxystyrene being 51.2 percent corresponding to a 4-acetoxystyrene yield of 51.0 percent. The yield calculation was determined on the basis of two moles of 4-acetoxystyrene being obtained per one mole of APMC-Ether and one mole of 4-acetoxystyrene being obtained per mole of APMC and APMC-Acetate.

EXAMPLE 2

A flask heated by hot oil was fitted with a chilled water overhead condenser, a thermowell with a thermocouple, an overhead stirrer and a vacuum pump. Crude APMC-Ether (20.0 grams) containing 78.2 weight percent APMC-Ether, 7.2 weight percent APMC and 3.9 weight percent APMC-Acetate was mixed in another flask with acetic anhydride (6.0 grams) and p-toluenesulfonic acid (0.027 grams). The resultant mixture was fed to the hot flask at a rate of 1.2 grams per minute. The hot oil temperature was maintained at about 220° C. to about 230° C. and the reaction mass temperature in the hot flask was maintained at about 180° C. to about 20020 C. The vacuum pump maintained a vacuum in the flask at about 80 mm Hg. The vacuum conditions caused the 4-acetoxystyrene and the acetic acid products to vaporize from the flask as soon as they were formed together with unreacted acetic anhydride. The vapors were condensed in the overhead condenser and collected in an overhead receiver. The residue and the catalyst were allowed to build up in the hot flask and were discarded after the cycle was completed.

At the end of the reaction, the total amount of residue removed from the flask was 3.7 grams and the product collected in the overhead receiver was 21.4 grams. The overhead product contained 62.9 weight percent 4-acetoxystyrene. The conversion of the crude APMC-Ether was 98.0 percent with the selectivity to 4-acetoxystyrene being 82.3 percent and corresponding to a 4-acetoxystyrene yield of 80.6 percent. The yield calculation was determined as described in Example 1.

EXAMPLE 3

A flask heated by hot oil was fitted with a chilled water overhead condenser, a thermowell with a thermocouple, an overhead stirrer and a vacuum pump. Crude APMC-Ether (20.0 grams) containing 76.7 weight percent APMC-Ether, 1.5 weight percent APMC and 4.6 weight percent APMC-Acetate was mixed in another flask. Ammonium bisulfate (0.03 grams) corresponding to 0.45 moles of ammonium bisulfate per 100 moles of APMC-Ether was added to said mixture. The resultant mixture was fed to the hot flask at a rate of 1.2 grams per minute. The hot oil temperature was maintained at about 220° C. to about 230° C. and the reaction mass temperature in the hot flask was maintained at about 180° C. to about 200° C. The vacuum pump maintained a vacuum in the flask at about 80 mm Hg. The vacuum conditions caused the 4-acetoxystyrene and acetic acid products to vaporize from the hot flask as soon as they were formed together with unreacted acetic anhydride. The vapors were condensed in the overhead condenser and collected in an overhead receiver. The residue and the catalyst were allowed to build up in the hot flask and were discarded after the cycle was completed.

At the end of the reaction, the total amount of residue removed from the flask was 2.4 grams and the product collected in the overhead receiver was 23.2 grams. The overhead product contained 65.3 weight percent 4-acetoxystyrene. The conversion of the crude APMC-Ether was 97.0 percent with the selectivity to 4-acetoxystyrene being 100 percent and corresponding to a 4-acetoxystyrene yield of 97.0 percent. The yield calculation was determined as described in Example 1.

EXAMPLE 4

A flask was fitted with a chilled water overhead condenser, a thermowell with a thermocouple, a magnetic stirrer and a vacuum pump. MPMC-ether (9.6 grams, 33.6 mmoles) was mixed with methanesulfonic acid (0.0062 grams, 0.065 mmole) and the mixture was added to the flask. The flask was heated to 140° C. with a hot oil bath and a vacuum was maintained at 3 mm Hg. The reaction was complete in 20 minutes. The product 4-methoxystyrene was distilled over as a colorless liquid. Seven (7.0) grams of product were obtained corresponding to a yield of 77 percent.

EXAMPLE 5

A one liter, three-necked flask was fitted with thermowell, a heating mantle, a mechanical stirrer and a Dean-Stark trap. A chilled water condenser, fitted with a pressure equalizing dropping funnel and a vacuum port was placed on top of the trap. The flask was charged with 100.1 grams of APMC, 297.2 grams of 1,2,4-trimethylbenzene and 38.1 grams (8.8 weight percent) potassium bisulfate. The reaction was heated to reflux at 90° C. under vacuum conditions (143 mm Hg). The reaction mass was continuously stirred for good mixing. After 100 minutes, the reaction was allowed to cool and was gravity filtered. The filtrate was shaken with 10.0 grams of sodium bicarbonate and was allowed to stand for one hour. The mixture was filtered and the filtrate was concentrated on a rotary evaporator at 1.0 mm Hg. The oil was shaken with an equal weight of petroleum ether to remove residual trimethylbenzene. The product was allowed to phase separate and the petroleum ether was stripped on the rotary evaporator at 143 mm Hg. Treatment with petroleum ether was repeated and, after rotovapping, the residual oil was analyzed by gas chromatography. The yield of APMC-Ether, based on APMC, was about 51 percent.

EXAMPLE 6

A three liter three-necked flask was fitted with a thermowell, a heating mantle, a mechanical stirrer and a Dean Stark trap. A chilled water condenser leading to a bubbler was placed on top of the trap. The flask was charged with 250.4 grams of APMC, 742.4 grams of toluene and 94.7 grams (8.7 weight percent) of potassium bisulfate. The reaction was heated to reflux at 111° C. After five (5.0) hours the reaction was sampled for gas chromatography analysis. The reaction was carried out under atmospheric pressure conditions (760 mm Hg). The conversion of APMC was 79.4 percent and the selectivity to APMC-Ether based on APMC 63.7 percent corresponding to a yield of APMC-Ether based on APMC of 51 percent.

EXAMPLE 7

A 100 milliliter two-necked flask was fitted with a thermowell, a magnetic stirrer and a vacuum port. The flask was charged with 59.35 grams of APMC and 5.69 grams (8.7 weight percent) of potassium bisulfate. The reaction mass was heated on an oil bath at 100° C. under 0.250 mm Hg. After 2.0 hours, the reaction was sampled for chromatography analysis. The yield of APMC-Ether, based on APMC, was about 84 percent.

EXAMPLE 8

A 100 milliliter flask equipped with a condenser, a magnetic stirrer and a hot-oil bath was charged with 4-methoxyphenylmethylcarbinol (MPMC) (50.0 grams) and p-toluenesulfonic acid (0.066 grams). The reaction mixture was heated to 80° C. and was stirred for 16 hours. The reaction mixture was then cooled to room temperature. Then it was dissolved in ethyl acetate (250 milliliters) and was washed with water three times with 250 milliliters of water each time. The organic layer was separated from the mixture and was dried over anhydrous magnesium sulfate. Then, it was concentrated on a rotary evaporator. The product was analyzed by gas chromotography which showed it to contain MPMC-Ether (70 percent), MPMC (17 percent) and 4-methoxystyrene (10 percent). This corresponds to an MPMC conversion of 83 percent. Distillation of this mixture under reduced pressure afforded pure MPMC-Ether.

While the invention is described with respect to specific embodiments, modifications thereof can be made by one skilled in the art without departing from the spirit of the invention. The details of said embodiments are not to be construed as limitations except to the extent indicated in the following claims.

What is claimed is:
1. A process, comprising the steps of:
contacting an arylalkanol of the formula

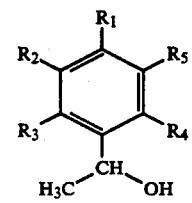

with an acid catalyst; and
heating the arylalkanol catalyst mixture to form a bisarylalkyl ether of the formula

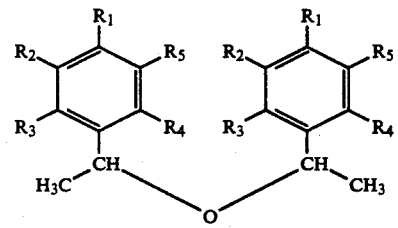

wherein $R_1$ is

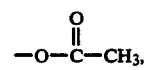

$-O-CH_3$, $-O-CH_2-CH_3$, halogen or $NO_2$;
and $R_2$, $R_3$, $R_4$ and $R_5$ are independently hydrogen, halogen or $C_1-C_4$ alkyl.
2. The process according to claim 1 wherein the heating step further forms water.
3. The process according to claim 2 wherein there is included the step of removing the water.
4. The process according to claim 2 wherein there is included the steps of:
contacting the water with an organic solvent; and codistilling the water and the organic solvent.
5. The process according to claim 2 wherein there is included the step of vaporizing the water.
6. The process according to claim 2 wherein there is included the step of providing a pressure which is sufficiently low to effect the vaporization of the water.
7. The process according to claim 1 wherein the acid catalyst is a weak catalyst.
8. The process according to claim 1 wherein the acid catalyst is potassium bisulfate.

9. The process according to claim 1 wherein the heating is at a temperature of about 80° C. to about 120° C.

10. The process according to claim 2 wherein there is included the step of maintaining a subatmospheric pressure which is sufficiently low to effect the vaporization of the water.

11. The process according to claim 1 wherein the arylalkanol is 4-acetoxyphenylmethylcarbinol and the bisarylalkyl ether is 4,4'-(oxydiethylidene)bisphenol diacetate.

12. The process according to claim 1 wherein the arylalkanol is 4-methoxyphenylmethylcarbinol and the bisarylalkyl ether is 4-4'-(oxydiethylidene)bisphenol dimethyl ether.

13. A process for producing a bisarylalkyl ether of the formula

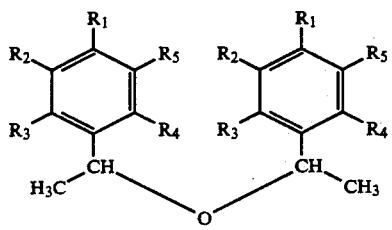

comprising the steps of:
mixing an arylalkanol of the formula

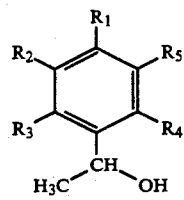

with an acid catalyst; and
subjecting the mixture to a temperature of about 80° C. to about 120° C.
wherein $R_1$ is

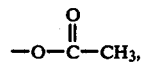

$-O-CH_3$, $-O-CH_2-CH_3$, halogen or NO; and $R_2$; $R_3$, $R_4$ and $R_5$ are independently hydrogen, halogen or $C_1-C_4$ alkyl.

14. A method of preparing a bisarylalkyl ether of the formula

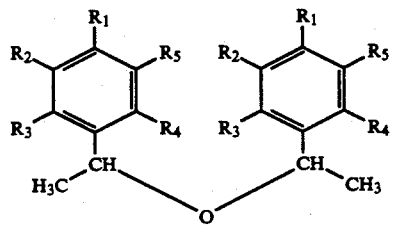

comprising the steps of:
interacting an arylalkanol of the formula

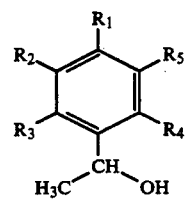

with an acid catalyst; and
heating the mixture to a temperature which is sufficient to convert the arylalkanol to the bisarylalkyl ether and water,
wherein $R_1$ is

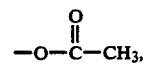

$-O-CH_3$, $-O-CH_2-CH_3$, halogen or $NO_2$; and $R_2$, $R_3$, $R_4$ and $R_5$ are independently hydrogen, halogen or $C_1-C_4$ alkyl.

* * * * *